United States Patent
Schwind et al.

(10) Patent No.: US 6,228,818 B1
(45) Date of Patent: *May 8, 2001

(54) ORGANOPHOSPHORYL BORATES AND LUBRICANTS AND AQUEOUS FLUIDS CONTAINING THE SAME

(75) Inventors: James J. Schwind, Eastlake; S. Q. Abbas Rizvi, Painesville; Stephen A. DiBiase, Euclid, all of OH (US)

(73) Assignee: The Lubrizol Corporation, Wickliffe, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/071,895

(22) Filed: Jun. 3, 1993

Related U.S. Application Data

(63) Continuation of application No. 07/804,273, filed on Dec. 6, 1991, now abandoned.

(51) Int. Cl.$^7$ ................ C01M 139/00; C01M 141/12
(52) U.S. Cl. .................. 508/187; 508/364; 508/322
(58) Field of Search .................. 252/46.6, 49.6; 508/187, 364, 322

(56) References Cited

U.S. PATENT DOCUMENTS

| | | | |
|---|---|---|---|
| 2,710,872 | 6/1955 | Thompson | 260/326.5 |
| 2,895,983 | 7/1959 | Asseff | 260/461 |
| 2,897,152 | 7/1959 | Elliott et al. | 252/47.5 |
| 2,965,664 | 12/1960 | Butler | 260/461 |
| 3,004,996 | 10/1961 | Arakelian et al. | 260/429.9 |
| 3,013,046 | 12/1961 | Denny | 260/261 |
| 3,031,401 | 4/1962 | Thayer | 252/46.7 |
| 3,182,021 | 5/1965 | Asseff | 252/46.6 |
| 3,213,020 | 10/1965 | Hopkins et al. | 252/32.7 |
| 3,213,021 | 10/1965 | Hopkins et al. | 252/32.7 |
| 3,213,022 | 10/1965 | Hopkins et al. | 252/32.7 |
| 3,291,734 | 12/1966 | Liao | 252/46.7 |
| 3,544,465 | * 12/1970 | Braid | 252/46.6 |
| 3,654,155 | * 4/1972 | Braid | 44/315 |
| 4,119,549 | 10/1978 | Davis | 252/45 |
| 4,119,550 | 10/1978 | Davis et al. | 252/45 |
| 4,191,659 | 3/1980 | Davis | 252/45 |
| 4,344,854 | 8/1982 | Davis et al. | 252/45 |
| 4,368,129 | 1/1983 | Horodysky et al. | 252/32.7 |
| 4,376,712 | 3/1983 | Horodysky et al. | 252/49.6 |
| 4,519,926 | * 5/1985 | Basalay et al. | 252/49.6 |
| 4,529,528 | 7/1985 | Horodysky | 252/49.6 |
| 4,536,306 | 8/1985 | Horodysky et al. | 252/32.7 |
| 4,755,311 | 7/1988 | Burjes et al. | 252/49.3 |
| 4,758,362 | 7/1988 | Butke | 252/47.5 |
| 4,784,780 | 11/1988 | Farng et al. | 252/32.7 |
| 4,925,983 | 5/1990 | Steckel | 564/3 |
| 4,997,969 | 3/1991 | Luciani | 558/240 |

OTHER PUBLICATIONS

International Search Report PCT/US 92/09780.

* cited by examiner

*Primary Examiner*—Jacqueline V. Howard
(74) *Attorney, Agent, or Firm*—Michael F. Esposito

(57) ABSTRACT

A borate ester represented by one of the following formulae:

$$((R_1)_2P(X_2)X_1R_2O)_3B \quad \text{or}$$

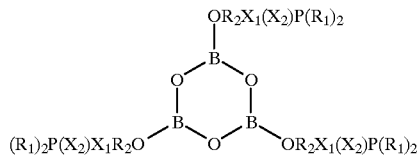

wherein each $R_1$ is independently hydrocarbyl, a hydrocarbyloxy or a hydrocarbylthio group or both $R_1$ on the same phosphorus atom taken together form a heterocyclic group; each $X_1$ and $X_2$ is independently an oxygen or sulfur; and each $R_2$ is independently a hydrocarbylene group. These reaction products are useful as lubricant additives for oil-based and water-based functional fluids. These materials act as anti-wear, extreme pressure and friction modifying agents.

22 Claims, No Drawings

ORGANOPHOSPHORYL BORATES AND LUBRICANTS AND AQUEOUS FLUIDS CONTAINING THE SAME

This is a continuation of applications Ser. No. 07/804,273 filed on Dec. 6, 1991 now abandoned.

FIELD OF THE INVENTION

This invention relates to borate esters of hydroxy-containing organophosphorus compounds, and lubricants and aqueous fluids containing borate esters.

INTRODUCTION TO THE INVENTION

Boron-, phosphorus-, and sulfur-containing compositions have been utilized in lubricating compositions as multi-functional additives such as extreme pressure and anti-wear agents.

U.S. Pat. No. 3,031,401 relates to lubricating oil composition containing amine salts of boronated partially esterified thiophosphates. These materials are the reaction product of an oil-soluble primary, secondary or tertiary alkyl, alkenyl, alkylol mono- or diamine and an anhydride prepared by reacting a partially esterified thiophosphoric acid with boric acid, boric oxide or an anhydride of boric acid and an aliphatic monocarboxylic acid.

U.S. Pat. No. 3,213,022 relates to lubricants containing metal phosphorodithioic-epoxide reaction products. These products are the reaction of a metal salt of phosphorodithioic acid and an organic epoxide.

U.S. Pat. No. 3,291,734 relates to boron-, phosphorus- and sulfur-containing additives and methods of making the same. These products were prepared by reacting an alpha-olefin with phosphorus pentasulfide to form an intermediate. The intermediate is then reacted with glycols or mixtures of glycols and alcohols to form a second intermediate, and finally the second intermediate is reacted with glycol borates or precursors thereof, such as a mixture of boric acid and glycol. These additives are useful in lubricating oils.

U.S. Pat. No. 4,368,129 relates to multi-functional lubricant additives which are metal salts of partially borated, partially phosphosulfurized polyols and hydroxy-containing esters. These additives are useful as friction reducing, anti-oxidant and copper strip passivating additives in lubricating media. The additives may be prepared by first partially phosphosulfurizing a hydroxyl-containing ester by reacting the hydroxyl-containing ester with a phosphosulfur compound such as phosphorus pentasulfide and then reacting the partially phosphosulfurized compound with a metal compound and thereafter borating the metal salt of the partially phosphosulfurized hydroxyl-containing ester.

U.S. Pat. No. 4,529,528 relates to boratedamine-phosphite reaction products and lubricants and fuels containing the same. The products are prepared by reacting a (2-hydroxyethyl)alkylamine or certain higher oxylated members, a dihydrocarbylphosphite in a boron compound. These additives are useful as friction reducers in lubricating compositions.

U.S. Pat. No. 4,536,306 relates to borated phosphorus-containing compounds and lubricant compositions containing the same. The compounds are prepared by reacting a phosphorus oxyhalide, a vicinal diol and a boron compound. These additives are useful in reducing friction in lubricating compositions.

U.S. Pat. No. 4,784,780 relates to lubricant additives comprising mixed hydroxyester or diol/phosphorodithioate-derived borate. The additives are prepared by reacting dialkyl or diaryl phosphorodithioate-derived alcohols and hydrocarbyl diols, hydroxyesters or related polydiols with a boronating agent.

SUMMARY OF THE INVENTION

This invention relates to a borate ester prepared by reacting a hydroxy-containing organophosphorus compound with a borating agent. In one embodiment, these reaction products may be represented by the following formulae alone or in combination:

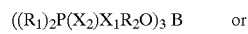

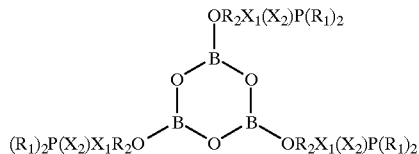

wherein each $R_1$ is independently hydrogen, a hydrocarbyl, hydrocarbyloxy or hydrocarbylthio group or both $R_1$ on the same phosphorus atom taken together form a heterocyclic group each $X_1$ and $X_2$ is independently an oxygen or sulfur; and each $R_2$ is independently a hydrocarbylene group, provided that at least one $R_1$ is other than hydrogen. These reaction products are useful as lubricant additives for oil-based and water-based functional fluids. These materials act as anti-wear, extreme pressure and friction modifying agents.

DETAILED DESCRIPTION OF THE INVENTION

The term "hydrocarbyl" includes hydrocarbon as well as substantially hydrocarbon groups. Substantially hydrocarbon describes groups which contain non-hydrocarbon substituents which do not alter the predominantly hydrocarbon nature of the group.

Examples of hydrocarbyl groups include the following:

(1) hydrocarbon substituents, that is, aliphatic (e.g., alkyl or alkenyl), alicyclic (e.g., cycloalkyl, cycloalkenyl) substituents, aromatic-, aliphatic- and alicyclic-substituted aromatic substituents and the like as well as cyclic substituents wherein the ring is completed through another portion of the molecule (that is, for example, any two indicated substituents may together form an alicyclic radical);

(2) substituted hydrocarbon substituents, that is, those substituents containing non-hydrocarbon groups which, in the context of this invention, do not alter the predominantly hydrocarbon nature of the substituent; those skilled in the art will be aware of such groups (e.g., halo (especially chloro and fluoro), hydroxy, alkoxy, mercapto, alkylmercapto, nitro, nitroso, sulfoxy, etc.);

(3) hetero substituents, that is, substituents which will, while having a predominantly hydrocarbon character within the context of this invention, contain an atom other than carbon present in a ring or chain otherwise composed of carbon atoms. Suitable heteroatoms will be apparent to those of ordinary skill in the art and include, for example, sulfur, oxygen, nitrogen, phosphorus and such substituents as, e.g., pyridyl, furyl, thienyl, imidazolyl, etc. In general, no more than about 2, preferably no more than one, non-hydrocarbon substituent will be present for every ten carbon atoms in the hydrocarbyl group. Typically, there will be no such non-hydrocarbon substituents in the hydrocarbyl group. Therefore, the hydrocarbyl group is purely hydrocarbon.

In one embodiment, the borate esters of the present invention may be represented by one of the following formulae alone or in combination:

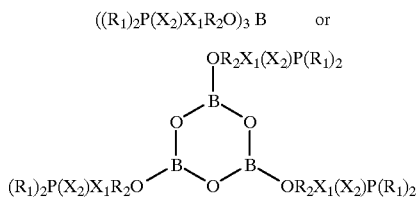

$((R_1)_2P(X_2)X_1R_2O)_3B$   or wherein each $R_1$ is independently hydrogen, a hydrocarbyl, a hydrocarbyloxy or a hydrocarbylthio group or both $R_1$ on the same phosphorus atom taken together form a heterocyclic group; each $X_1$ and $X_2$ is independently an oxygen or sulfur; and each $R_2$ is independently a hydrocarbylene group, provided that when one $R_1$ is hydrogen, the other $R_1$ is other than hydrocarbon.

Preferably, each $R_1$ is independently hydrogen, an alkyl, aryl, alkoxy, aryloxy, alkylthio or arylthio group, with an alkoxy or aryloxy group being more preferred. In one embodiment, each $R_1$ independently contains from 1, or about 3, to about 30 or about 24, or about 18 carbon atoms. Each $R_1$ may be independently derived from any of the monohydroxy organic compounds listed below. Examples of $R_1$ include propyl, propoxy, propylthio, butyl, butoxy, butylthio, amyl, amyloxy, amylthio, hexyl, hexyloxy and hexylthio groups. The above list is meant to include all isomeric arrangements of the above groups. For instance, butyl is meant to include isobutyl, sec-butyl, n-butyl, etc. In a preferred embodiment, one $R_1$ is a isopropoxy or isobutoxy group and the other $R_1$ is an amyloxy or a methylamyloxy group.

When $R_1$ is an aryl, aryloxy or arylthio group, $R_1$ contains from 6 to about 18 carbon atoms, more preferably 6 to about 10. Examples of aromatic $R_1$ groups include cresyl, cresyloxy, cresylthio, xylyl, xylyloxy, xylylthio, heptylphenol, and heptylphenolthio groups, preferably cresyl or cresyloxy groups.

$X_1$ and $X_2$ are each independently oxygen or sulfur, preferably sulfur. In one embodiment, $X_1$ or $X_2$ is sulfur and correspondingly $X_2$ or $X_1$ is oxygen. In another embodiment, both $X_1$ and $X_2$ are sulfur or both $X_1$ and $X_2$ are oxygen. As described, the organophosphoryl borates of the present invention are prepared by reacting a hydroxy-containing organophosphorus compound with a boron compound. The hydroxy-containing organophosphorus compound is prepared by reacting an organophosphorus acid with an epoxide.

The organophosphorus acids useful in preparing the hydroxy-containing organophosphorus compounds include organo-phosphoric, phosphinic, thiophosphoric, thiophosphinic, or thiophosphonic acids. Use of the terms thiophosphoric, thiophosphonic and thiophosphinic acids is meant to encompass monothio as well as dithio forms of these acids. In one embodiment, the organophosphorus compound is a mono, di, tri or tetrathiophosphoric acid. The organophosphorus acids are known compounds and may be prepared by known methods. Preferably, the organophosphorus acid is a organodithiophosphoric acid.

Organodithiophosphoric acids are known compounds and may be prepared by the reaction of a mixture of hydroxy-containing organic compounds such as alcohols and phenols with a phosphorus sulfide such as $P_2S_5$. The organodithiophosphoric acids generally are prepared by reacting from about 3 to 5 moles, more generally 4 moles or the hydroxy-containing organic compound (alcohol or phenol) with one mole or phosphorus pentasulfide in an inert atmosphere at temperatures from about 50° C. to about 200° C. with the evolution of hydrogen sulfide. The reaction normally is completed in about 1 to 3 hours.

Monohydroxy organic compounds useful in the preparation of the organophosphorus acids include alcohols, xylenols, alkyl xylenols, phenols and alkyl phenols including their substituted derivatives, e.g., nitro-, halo-, alkoxy-, hydroxy-, carboxy-, etc. Suitable alcohols include, for example, ethanol, n-propanol, isopropanol, n-butanol, 2-butanol, 2-methylpropanol, n-pentanol, 2-pentanol, 3-pentanol, 2-methylbutanol, 3-methyl-2-pentanol, n-hexanol, 2-hexanol, 3-hexanol, 4-methyl-2-pentanol, 2-methyl-3-pentanol, cyclohexanol, chlorocyclohexanol, methyl-cyclohexanol, heptanol, 2-ethylhexanol, n-octanol, nonanol, dodecanol, etc. The phenols include alkyl phenols and substituted phenols such as phenol, chlorophenol, bromophenol, nitrophenol, methoxyphenol, decylphenol, dodecylphenol, and commercially available mixtures of phenols. The aliphatic alcohols containing from about 4 to 6 carbon atoms are particularly useful in preparing the organophosphorus and preferably organodithiophosphorus acids.

In one embodiment, the mixture of alcohols and/or phenols is reacted with phosphorus pentasulfide. Typical mixtures of alcohols and phenols which can be used in the preparation of organophosphorus acids include: isobutyl and primary-amyl alcohols; sec-butyl and primary-amyl alcohols; propyl and primary-hexyl alcohols; isobutyl alcohol, primary-amyl alcohol and 2-methyl-1-butanol; phenol and primary-amyl alcohol; phenol and cresol, etc.

In another embodiment, the organophosphorus acid is an organomonothiophosphorus acid. Organomonothiophosphorus acids are known compounds and may be prepared by reacting an organodithiophosphorus acid with water or steam causing hydrolysis of the organodithiophosphorus acid to organomonothiophosphorus acid. Alternatively, the organomonothiophosphorus acid may be prepared by reacting an organophosphite compound with a sulfur compound, optionally in the presence of an amine or an amide. Generally, the reaction occurs at a temperature from about 100° C. to about 250° C. in the presence or the absence of an inert diluent. The reaction of an organophosphite with sulfur is described in U.S. Pat. Nos. 4,755,311, the disclosure of which is hereby incorporated by reference.

In another embodiment, the organophosphorus acid may be prepared by reacting one or more of the hydroxy compounds with a phosphorus pentoxide ($P_2O_5$). The hydroxy compounds may be reacted with the phosphorus pentoxide at ratios to form mono or diorganophosphoric acid. The hydroxy compounds may be reacted with phosphorus pentoxide at a temperature from about 75° C. to about 250° C.

The organophosphorus acids are then reacted with an epoxide to form the hydroxy-containing organophosphorus compounds. The epoxide is preferably an epoxide derived from an olefin. The epoxides generally contain from 2, preferably 3 to about 30, preferably to about 24, more preferably to about 18 carbon atoms. These epoxides are preferably derived from alpha-olefins (sometimes referred to as mono-1-olefins) or isomerized alpha-olefins. Examples of the epoxides include epoxides of 1-octene, 1-nonene, 1-decene, 1-dodecene, 1-tridecene, 1-tetradecene, 1-pentadecene, 1-hexadecene, 1-heptadecene, 1-octadecene.

1-nonadecene, 1-eicosene, 1-heneicosene, etc. Commercially available alpha-olefin fractions which may be used to form epoxides include the $C_{15-18}$ alpha-olefins, $C_{14-16}$ alpha-olefins, $C_{14-18}$ alpha-olefins, $C_{16-18}$ alpha-olefins, $C_{16-20}$ alpha-olefins, $C_{22-28}$ alpha-olefins, etc. The $C_{16}$ and $C_{16-18}$ alpha-olefins are particularly preferred.

Specific examples of epoxides include ethylene oxide, propylene oxide, butylene oxide, cyclohexene oxide, styrene oxide, decene oxide, tetradecene oxide, hexadecene oxide and octadecene oxide.

The above organophosphorus acids are reacted with the above epoxides at a temperature below the decomposition temperature of the individual reactants or reaction mixture, preferably at a temperature below 150° C., more preferably from about 0° C., or room temperature to about 50° C. The reaction of the organophosphorus acid and epoxide is exothermic. Preferably, the organophosphorus acid is blown with an inert gas such as nitrogen, to remove any impurities, such as hydrogen sulfide from an organodithiophosphoric acid. Generally, the epoxide is added to the organophosphorus acid. The reaction may be conducted in the presence of an inert diluent such as toluene, xylene, etc.

Boron Compounds

The above hydroxy-containing organophosphorus compounds are reacted with boron compounds to form the borate esters of the present invention. The boron compounds include boron oxide, boron oxide hydrate, boron trioxide, boron trifluoride, boron tribromide, boron trichloride, boron acids such as boronic acid (i.e., alkyl-B(OH)$_2$ or aryl-B(OH)$_2$), including methyl boronic acid, phenyl-boronic acid, cyclohexyl boronic acid, p-heptylphenyl boronic acid and dodecyl boronic acid, boric acid (i.e., $H_3BO_3$), tetraboric acid (i.e., $H_2B_4O_7$), metaboric acid (i.e., $HBO_2$), boron anhydrides, boron amides and various esters of such boron acids. The use of complexes of boron trihalide with ethers, organic acids, inorganic acids, or hydrocarbons is a convenient means of introducing the boron reactant into the reaction mixture. Such complexes are known and are exemplified by boron-trifluoride-triethyl orthoester, boron trifluoride-phosphoric acid, boron trichloride-chloroacetic acid, boron tribromide-dioxane, and boron trifluoride-methyl ethyl ether complexes.

The boron acid esters include especially mono-, di-, and tri-organic esters of boric acid with alcohols or phenols such as, e.g., methanol, ethanol, propanol, 1-octanol, benzyl alcohol, ethylene glycol, glycerol, Cellosolve, phenol. Lower alcohols, 1,2-glycols, and 1,3-glycols, i.e., those having less than about 8 carbon atoms are especially useful for preparing the boric acid esters for the purpose of this invention. Methods for preparing the boric acid esters are known and disclosed in the art (such as "Chemical Reviews," pp. 959–1064, Vol. 56).

From one to about 3 equivalents of hydroxy-containing organophosphorus compounds are reacted with one equivalent of boron compound. The equivalents of hydroxycontaining organophosphorus compounds are determined by dividing the formula weight of the hydroxy-containing organophosphorus compound by the number of hydroxyl groups. The equivalents of boron compound are determined by dividing the formula weight of the boron compound by the number of boron atoms. The hydroxy-containing organophosphorus compound is reacted with a boron compound at a temperature from about 60° C., preferably about 80° C. to the decomposition temperature of the reactants or reaction mixture, preferably to about 150° C., more preferably to about 110° C. The reaction may occur with or without a diluent, such as xylene, toluene, kerosene, or mineral oils.

The following examples relate to hydroxy organophosphoryl borates of the present invention. Unless otherwise indicated in the following examples as well as in the specification and claims, all parts and percentages are by weight, all temperatures are degrees celsius, and pressure is atmospheric pressure.

EXAMPLE 1

A reaction vessel is charged with 1661 parts (4.68 equivalents) of di-(methylamyl)dithiophosphoric acid. The reaction vessel is sparged with nitrogen at 0.5 standard cubic foot per hour for 30 minutes. Propylene oxide (277 parts, 4.77 equivalents) is added to the reaction vessel while maintaining the reaction temperature below 60° C. The reaction temperature is maintained at 60° C. for 30 minutes after completion of the addition of propylene oxide. Boric acid (99 parts, 1.59 equivalents) is added to the reaction mixture, and the reaction is heated to 90° C. The reaction temperature is maintained at 90° C. for 3 hours under a partial vacuum (160 millimeters of mercury) while 60 milliliters of water are collected. The reaction mixture is vacuum stripped to 90° C. and 50 millimeters of mercury. The reaction mixture is filtered through diatomaceous earth and the filtrate is the desired product. The desired product contains 7.55% phosphorus (8.08% theoretical), 0.86% boron (0.9% theoretical) and 15.33% sulfur (16.59% theoretical).

EXAMPLE 2

A reaction vessel is charged with 2125 parts (5.0 equivalents) of di(2-ethylhexyl)dithiophosphoric acid. The reaction vessel is sparged with nitrogen at 0.5 standard cubic foot per hour for 1.5 hours. Hexadecenyl alpha-olefin epoxide (1217 parts, 5.0 equivalents) is added to the reaction vessel; and the reaction is exothermic. The reaction mixture is heated at 90° C. and the temperature is maintained for two hours. Additional hexadecenyl alpha-olefin epoxide (122 grams, 0.5 equivalents) is added to the reaction mixture. The reaction mixture is cooled to room temperature. The neutralization number of the reaction mixture is 2.7. Boric acid (105 parts, 1.68 equivalents) and 300 milliliters of toluene are added to the reaction mixture. The reaction mixture is heated to toluene reflux while 50 millimeters of water are collected. The reaction mixture is vacuum stripped to 105° C. and 35 millimeters of mercury. The reaction mixture is filtered through diatomaceous earth and the filtrate is the desired product. The desired product contains 4.49% phosphorus (4.5% theoretical), 0.43% boron (0.53% theoretical), and 9.69% sulfur (10.0% theoretical).

The following examples 3–9 are prepared by following the procedure of Example 1. The phosphorus acid is reacted with the epoxide on an equal molar basis to form an intermediate. The intermediate is then further reacted with boric acid in an equivalent ratio described in Table I:

TABLE I

| Example Number | Phosphorus Acid | Epoxide | Equivalents of Intermediate Boric Acid |
|---|---|---|---|
| 3 | Diisooctyl dithiophosphoric acid | Propylene oxide | (1:1) |
| 4 | Diisooctyl dithiophosphoric acid | Propylene oxide | (3:1) |
| 5 | Diisooctyl dithiophosphoric acid | Propylene oxide | (1.5:1) |

TABLE I-continued

| Example Number | Phosphorus Acid | Epoxide | Equivalents of Intermediate Boric Acid |
|---|---|---|---|
| 6 | Isopropyl methylamyl dithiophosphoric acid (60:40% mole) | Dodecene oxide | (3:1) |
| 7 | Isopropyl methylamyl dithiophosphoric acid (60:40% mole) | Dodecene oxide | (1:1) |
| 8 | Diheptylphenyl dithiophosphoric acid | Hexadecene oxide | (1:1) |
| 9 | Diheptylphenyl dithiophosphoric acid | Hexadecene oxide | (2:1) |

Lubricants

As previously indicated, the organophosphoryl borates of this invention are useful as additives for lubricants in which they can function primarily as anti-wear, extreme pressure and/or friction modifying agents. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

In one embodiment, the organophosphoryl borates of the present invention are used in lubricating compositions together with a sulfurized organic composition or a dithiocarbamate-containing compound. In this embodiment, the sulfurized organic compositions or the dithiocarbamate-containing compound is present in an amount from about 0.05%, or about 1%, or about 2% up to about 10%, or to about 7%, or to about 6% by weight of the lubricating composition. The sulfurized organic compositions include mono- or polysulfide compositions or mixtures thereof. The sulfurized organic compositions are generally characterized as having sulfide linkages containing an average from 1, or from about 2, or from about 3 up to about 10, or to about 8, or to about 4 sulfur atoms. In one embodiment, the sulfurized organic compositions are polysulfide compositions generally characterized as di- tri- or tetrasulfide compositions.

Materials which may be sulfurized to form the sulfurized organic compositions include oils, fatty acids or esters, olefins or polyolefins made thereof, terpenes, or Diels-Alder adducts.

Oils which may be sulfurized are natural or synthetic oils including mineral oils, lard oil, carboxylic acid esters derived from aliphatic alcohols and fatty acids or aliphatic carboxylic acids (e.g., myristyl oleate and oleyl oleate), sperm whale oil and synthetic sperm whale oil substitutes, and synthetic unsaturated esters or glycerides.

Fatty acids generally contain from about 4 to about 22 carbon atoms. The unsaturated fatty acids generally contained in the naturally occurring vegetable or animal fats and oils may contain one or more double bonds and such acids include palmitoleic acid, oleic acid, linoleic acid, linolenic acid, and erucic acid. The unsaturated fatty acids may comprise mixtures of acids such as those obtained from naturally occurring animal and vegetable oils such as lard oil, tall oil, peanut oil, soybean oil, cottonseed oil, sunflower seed oil, or wheat germ oil. Tall oil is a mixture of rosin acids, mainly abietic acid, and unsaturated fatty acids, mainly oleic and linoleic acids. Tall oil is a by-product of the sulfate process for the manufacture of wood pulp.

The unsaturated fatty acid esters are the fatty oils, that is, naturally occurring esters of glycerol with the fatty acids described above, and synthetic esters of similar structure. Examples of naturally occurring fats and oils containing unsaturation include animal fats such as Neat's-foot oil, lard oil, depot fat, beef tallow, etc. Examples of naturally occurring vegetable oils include cottonseed oil, corn oil, poppyseed oil, safflower oil, sesame oil, soybean oil, sunflower seed oil and wheat germ oil.

The fatty acid esters also may be prepared from aliphatic olefinic acids of the type described above such as oleic acid, linoleic acid, linolenic acid, and erucic acid by reaction with alcohols and polyols. Examples of aliphatic alcohols which may be reacted with the above-identified acids include monohydric alcohols such as methanol, ethanol, n-propanol, isopropanol, the butanols, etc.; and polyhydric alcohols including ethylene glycol, propylene glycol, trimethylene glycol, neopentyl glycol, glycerol, etc.

The olefinic compounds which may be sulfurized are diverse in nature. They contain at least one olefinic double bond, which is defined as a non-aromatic double bond; that is, one connecting two aliphatic carbon atoms. In its broadest sense, the olefin may be defined by the formula $R^{*1}R^{*2}C=CR^{*3}R^{*4}$, wherein each of $R^{*1}$, $R_{*2}$, $R_{*3}$ and $R^{*4}$ is hydrogen or an organic group. In general, the $R^*$ groups in the above formula which are not hydrogen may be satisfied by such groups as $-C(R^{*5})_3$, $-COOR^{*5}$, $-CON(R^{*5})_2$, $-COON(R^{*5})_4$, $-COOM$, $-CN$, $-X$, $-YR^{*5}$ or $-Ar$, wherein:

each $R^{*5}$ is independently hydrogen, alkyl, alkenyl, aryl, substituted alkyl, substituted alkenyl or substituted aryl, with the proviso that any two $R^{*5}$ groups can be alkylene or substituted alkylene whereby a ring of up to about 12 carbon atoms is formed;

M is one equivalent of a metal cation (preferably Group I or II, e.g., sodium, potassium, barium, calcium);

X is halogen (e.g., chloro, bromo, or iodo);

Y is oxygen or divalent sulfur;

Ar is an aryl or substituted aryl group of up to about 12 carbon atoms.

Any two of $R^{*1}$, $R_{*2}$, $R^{*3}$ and $R^{*4}$ may also together form an alkylene or substituted alkylene group; i.e., the olefinic compound may be alicyclic.

The olefinic compound is usually one in which each R group which is not hydrogen is independently alkyl, alkenyl or aryl group. Monoolefinic and diolefinic compounds, particularly the former, are preferred, and especially terminal monoolefinic hydrocarbons; that is, those compounds in which $R^{*3}$ and $R^{*4}$ are hydrogen and $R^{*1}$ and $R_{*2}$ are alkyl or aryl, especially alkyl (that is, the olefin is aliphatic) having 1 to about 30, preferably 1 to about 16, more preferably 1 to about 8, and more preferably 1 to about 4 carbon atoms. Olefinic compounds having about 3 to 30 and especially about 3 to 16 (most often less than 9) carbon atoms are particularly desirable.

Isobutene, propylene and their dimers, trimers and tetramers, and mixtures thereof are especially preferred olefinic compounds. Of these compounds, isobutylene and diisobutylene are particularly desirable because of their availability and the particularly high sulfur containing compositions which can be prepared therefrom.

In another embodiment, the sulfurized organic compound is a sulfurized terpene compound. The term "terpene compound" as used in the specification and claims is intended to include the various isomeric terpene hydrocarbons having the empirical formula $C_{10}H_{16}$, such as contained in turpentine, pine oil and dipentenes, and the various synthetic and naturally occurring oxygen-containing derivatives. Mixtures of these various compounds generally will be utilized, especially when natural products such as pine oil and turpentine are used. Pine oil, for example, which is obtained by destructive distillation of waste pine wood with superheated steam comprises a mixture of terpene derivatives such as alpha-terpineol, beta-terpineol, alpha-fenchol, camphor, borneol/isoborneol, fenchone, estragole, dihydro alpha-terpineol, anethole, and other mono-terpene hydrocarbons. The specific ratios and amounts of the various components in a given pine oil will depend upon the particular source and the degree of purification. A group of pine oil-derived products available commercially from Hercules Incorporated. It has been found that the pine oil products generally known as terpene alcohols available from Hercules Incorporated are particularly useful in the preparation of the sulfurized products of the invention. Examples of such products include alpha-Terpineol containing about 95–97% of alpha-terpineol, a high purity tertiary terpene alcohol mixture typically containing 96.3% of tertiary alcohols; Terpineol 318 Prime which is a mixture of isomeric terpineols obtained by dehydration of terpene hydrate and contains about 60–65 weight percent of alpha-terpineol and 15–20% beta-terpineol, and 18–20% of other tertiary terpene alcohols. Other mixtures and grades of useful pine oil products also are available from Hercules under such designations as Yarmor 302, Herco pine oil, Yarmor 302W, Yarmor F and Yarmor 60.

In one embodiment, sulfurized olefins are produced by (1) reacting sulfur monochloride with a stoichiometric excess of a low carbon atom olefin, (2) treating the resulting product with an alkali metal sulfide in the presence of free sulfur in a mole ratio of no less than 2:1 in an alcohol-water solvent, and (3) reacting that product with an inorganic base. This procedure is described in U.S. Pat. No. 3,471,404, and the disclosure of U.S. Pat. No. 3,471,404 is hereby incorporated by reference for its discussion of this procedure for preparing sulfurized olefins and the sulfurized olefins thus produced. Generally, the olefin reactant contains from about 2 to 5 carbon atoms and examples include ethylene, propylene, butylene, isobutylene, amylene, etc.

The sulfurized olefins which are useful in the compositions of the present invention also may be prepared by the reaction, under superatmospheric pressure, of olefinic compounds with a mixture of sulfur and hydrogen sulfide in the presence of a catalyst, followed by removal of low boiling materials. This procedure for preparing sulfurized compositions which are useful in the present invention is described in U.S. Pat. No. 4,191,659, the disclosure of which is hereby incorporated by reference for its description of the preparation of useful sulfurized compositions. In one embodiment, the sulfurized olefin is prepared by reacting 16 moles of isobutylene with 16 moles of sulfur and 8 moles of hydrogen sulfide.

In another embodiment, the sulfurized organic composition is at least one sulfur-containing material which comprises the reaction product of a sulfur source and at least one Diels-Alder adduct in a molar ratio of at least 0.75:1. Generally, the molar ratio of sulfur source to Diels-Alder adduct is in a range of from about 0.75 to about 4.0, preferably about 1 to about 2.0, more preferably about 1 to about 1.8. In one embodiment the molar ratio of sulfur to adduct is from about 0.8:1 to 1.2:1.

The Diels-Alder adducts are a well-known, art-recognized class of compounds prepared by the diene synthesis or Diels-Alder reaction. A summary of the prior art relating to this class of compounds is found in the Russian monograph, *Dienovyi Sintes,* Izdatelstwo Akademii Nauk SSSR, 1963 by A. S. Onischenko. (Translated into the English language by L. Mandel as A. S. Onischenko, *Diene Synthesis,* N.Y., Daniel Davey and Co., Inc., 1964.) This monograph and references cited therein are incorporated by reference into the present specification.

Basically, the diene synthesis (Diels-Alder reaction) involves the reaction of at least one conjugated diene with at least one ethylenically or acetylenically unsaturated compound, these latter compounds being known as dienophiles. Piperylene, isoprene, methylisoprene, chloroprene, and 1,3-butadiene are among the preferred dienes for use in preparing the Diels-Alder adducts.

In addition to these linear 1,3-conjugated dienes, cyclic dienes are also useful as reactants in the formation of the Diels-Alder adducts. Examples of these cyclic dienes are the cyclopentadienes, fulvenes, 1,3-cyclohexadienes, 1,3-cycloheptadienes, 1,3,5-cycloeptatrienes, cyclooctatetraene, and 1,3,5-cyclononatrienes. Various substituted derivatives of these compounds enter into the diene synthesis.

Dienophiles, useful in preparing the Diels-Alder adducts, include those having at least one electron-accepting groups selected from groups such as formyl, cyano, nitro, carboxy, carbohydrocarbyloxy, hydrocarbyl- carbonyl, hydrocarbylsulfonyl, carbamyl, acylcarbamyl, N-acyl-N-hydrocarbylcarbamyl, N-hydrocarbylcarbamyl, and N,N-dihydrocarbylcarbamyl. The dienophiles include: nitroalkenes; alpha,beta-ethylenically unsaturated carboxylic esters, acids or amides; ethylenically unsaturated aldehydes and vinyl ketones. Specific examples of dienophiles include 1-nitrobutene-1, alkylacrylates, acrylamide, dibutylacrylamide, methacrylamide, crotonaldehyde; crotonic acid, dimethyldivinyl ketone, methylvinyl ketone and the like.

Another class of dienophiles are those having at least one carboxylic ester group represented by —C(O)O—$R_o$ where $R_o$ is the residue of a saturated aliphatic alcohol of up to about 40 carbon atoms, the aliphatic alcohol from which —$R_o$ is derived can be a mono or polyhydric alcohol such as alkyleneglycols, alkanols, aminoalkanols, alkoxy-substituted alkanols, ethanol, ethoxy ethanol, propanol, beta-diethylamino-ethanol; dodecyl alcohol, diethylene glycol, tripropylene glycol, tetrabutylene glycol, hexanol, octanol, isooctyl alcohol, and the like. In this especially preferred class of dienophiles, not more than two —C(O)—O—$R_o$ groups will be present, preferably only one —C(O)—O—$R_o$ group.

In addition to the ethylenically unsaturated dienophiles, there are many useful acetylenically unsaturated dienophiles such as propiolaldehyde, methyl-ethynylketone, propylethynylketone, propenylethynylketone, propiolic acid, propiolic acid nitrile, ethyl-propiolate, tetrolic acid, propargylaldehyde, acetylene-dicarboxylic acid, the dimethyl ester of acetylenedicarboxylic acid, dibenzoylacetylene, and the like.

Cyclic dienophiles include cyclopentenedione, coumarin, 3-cyano-coumarin, dimethyl maleic anhydride, 3,6-endomethylene-cyclohexenedicarboxylic acid, etc. With the exception of the unsaturated dicarboxylic anhydrides derived from linear dicarboxylic acids (e.g., maleic anhydride, methylmaleic anhydride, chloromaleic anhydride), this class of cyclic dienophiles are limited in commercial usefulness due to their limited availability and other economic considerations.

Normally, the adducts involve the reaction of equimolar amounts of diene and dienophile. However, if the dienophile has more than one ethylenic linkage, it is possible for additional diene to react if present in the reaction mixture.

The sulfur-containing Diels-Alder adducts are readily prepared by heating a mixture of a sulfur source, preferably sulfur and at least one of the Diels-Alder adducts of the types discussed hereinabove at a temperature within the range of from about 110° C. to just below the decomposition temperature of the Diels-Alder adducts. Temperatures within the range of about 110° to about 200° C. will normally be used.

The reaction can be conducted in the presence of suitable inert organic solvents such as mineral oils, alkanes of 7 to 18 carbons, etc., although no solvent is generally necessary. After completion of the reaction, the reaction mass can be filtered and/or subjected to other conventional purification techniques. An example of a useful sulfurized Diels-Alder adduct is a sulfurized reaction product of butadiene and butyl-acrylate.

The dithiocarbamate-containing compounds may be dithiocarbamate esters, dithiocarbamate amides, dithiocarbamic ethers, or alkylene-coupled dithiocarbamates.

Generally, a dithiocarbamic acid or salt is reacted with an unsaturated amide, ether, or ester to form the dithiocarbamate-containing compounds.

The dithiocarbamates used in making the dithiocarbamate-containing compound are prepared by reacting an amine with carbon disulfide. The amines are secondary amines. Specific amines include dimethyl amine, diethyl amine, dipropyl amine, dibutyl amine, diamyl amine, dihexyl amine and diheptyl amine. Non-symmetrical amines may also be used and they include methylethyl amine, ethylbutyl amine, ethylamyl amine and the like. The unsaturated amide, ether, or esters are preferably alpha, beta unsaturated compounds. The carboxylic esters include acrylate, methacrylate, maleate, fumarate, or itaconate esters. These esters have from 1, or about 2, up to about 30, or to about 24, or to about 18 carbon atoms in the ester group. Preferably, these compounds include methylacrylate, ethylacrylate, 2-ethylhexylacrylate, 2-hydroxyethylacrylate, ethylmethacrylate, 2-hydroxyethylmethacrylate, 2-hydroxypropylmethacrylate, 2-hydroxypropylacrylate, an acrylamide, and acrylonitrile, preferably acrylamides. Acrylamides include acrylamide, methacrylamide, bisacrylamide, bismethacrylamide, bismethyleneacrylamide, N-hydroxymethylacrylamide, N-mercaptomethylacrylamide, N-(methyl, ethyl, thioether) acrylamide, and N-(methyl, ethyl, ether) acrylamide.

The dithiocarbamates are reacted with the unsaturated compounds at a temperature of about 25° C. to about 125° C., preferably about 50° C. to about 100° C., more preferably 70° C. to about 90° C. The reaction may be carried out in the presence or absence of a solvent. Solvents include hydrocarbons such as toluene, xylene, hexane, heptane, kerosene, fuel oil or oils of lubricating viscosity as well as chlorohydrocarbons including chloroform, carbon tetrachloride and the like. Alcohols may also be used, such as methanol, ethanol, bropanol, butanol, 2-ethylhexanol and the like. In one embodiment, the dithiocarbamate containing composition is derived from the reaction product of a diamyl amine with carbon disulfide which forms a dithiocarbamic acid which is ultimately reacted with a acrylamide. In another embodiment, the dithiocarbamate acid is formed from diethylamine and carbon disulfide. The resulting dithiocarbamic acid is then reacted with methyl acrylate.

In one embodiment, the dithiocarbamate-containing compound is an alkylene-coupled dithiocarbamate. Alkylene-coupled dithiocarbamates may be represented by the formula

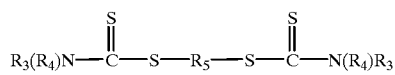

wherein $R_3$, $R_4$ and $R_5$ are defined below.

Each $R_3$ is independently a hydrogen; a hydrocarbyl group having from 1 to about 18 carbon atoms, preferably 1 to about 10, more preferably 1 to about 6; or $R_3$ taken together with $R_4$ and the nitrogen atom form a five, six or seven member heterocyclic group. Preferably, each $R_3$ is hydrogen or an alkyl group, more preferably hydrogen or a propyl, butyl, amyl or hexyl group, more preferably a butyl group. The above list encompasses all isomeric arrangements these groups, including isopropyl, n-propyl, sec-butyl, isobutyl, and n-butyl.

Each $R_4$ is independently a hydrocarbyl group having from 1 to about 18 carbon atoms, or $R_4$ taken together with $R_3$ and the nitrogen atom form a five, six or seven member heterocyclic group. When $R_4$ is a hydrocarbyl group, it is defined the same as when $R_3$ is a hydrocarbyl group.

When $R_3$ and $R_4$ are taken together with a nitrogen atom to form a five, six or seven member heterocyclic group, the heterocyclic group is a pyrrolidinyl, a piperidinyl, a morpholinyl or a piperazinyl group. The heterocyclic group may contain one or more, preferably one to three alkyl substituents on the heterocyclic ring. The alkyl substituents preferably contain from about one to about six carbon atoms. Examples of heterocyclic groups include 2-methylmorpholinyl, 3-methyl-5-ethylpiperidinyl, 3-hexylmorpholinyl, tetramethylpyrrolidinyl, piperazinyl, 2,5-dipropylpiperazinyl, piperidinyl, 2-butylpiperazinyl, 3,4,5-triethylpiperidinyl, 3-hexylpyrrolidinyl, and 3-ethyl-5-isopropylmorpholinyl groups. Preferably, the heterocyclic group is a pyrrolidinyl or piperidinyl group.

In one embodiment, each $R_3$ is independently a hydrogen, or a hydrocarbyl group and each $R_4$ is independently a hydrocarbyl group. In another embodiment, one $R_3$ and $R_4$ taken together with a nitrogen atom form a five, six or seven member heterocyclic group while the other $R_3$ is independently a hydrogen or a hydrocarbyl group and the other $R_4$ is a hydrocarbyl group. In another embodiment, each $R_3$ and $R_4$ taken together with the nitrogen atom form a five, six or seven member heterocyclic group.

$R_5$ is a hydrocarbylene group having from 1 to about 10 carbon atoms, preferably 1 to about 4, more preferably 1 or 2. Preferably, $R_5$ is an alkylene, arylene, alkarylene, or arylalkylene. In one embodiment, $R_5$ is an alkylene group, preferably, a methylene or ethylene group, more preferably methylene.

In one embodiment, $R_5$ is an arylene group, alkarylene group, or arylalkylene group having from 6 to about 10 carbon atoms, preferably 6 to about 8. Preferably, $R_5$ is a phenylmethylene, phenylethylene, phenyldiethylene, phenylene, or tolylene group.

The alkylene-coupled dithiocarbamates useful in the present invention may be prepared by the reaction of a salt of a dithiocarbamic acid with a suitable dihalogen containing hydrocarbon in the presence of a suitable reaction medium. Suitable reaction media include alcohols, such as ethanol and methanol; ketones, such as acetone or methylethylketone; ethers, such as dibutylether or dioxane; and hydrocarbons, such as petroleum ether, benzene and toluene. The reaction is generally carried out at a temperature within the range of about 25° C. to about 150° C., more preferably about 25° C. to about 100° C.

U.S. Pat. No. 3,876,550 issued to Holubec describes lubricant compositions containing alkylene dithiocarbamic compounds. U.S. Pat. Nos. 1,726,647 and 1,736,429, issued to Cadwell describe, phenylmethylene bis (dithiocarbamates) and methods of making the same. These patents are incorporated by reference for their teachings related to dithiocarbamate compounds and methods for preparing the same. In one embodiment, the alkylene-coupled dithiocarbamate is derived from dithiocarbamic acids formed from di-n-butyl amine, carbon disulfide and methylene dichloride.

The invention also contemplates the use of other additives in combination with the organophosphoryl borates of this invention. Such additives include, for example, detergents and dispersants of the ash-producing or ashless type, corrosion- and oxidation-inhibiting agents, pour point depressing agents, extreme pressure agents, anti-wear agents, color stabilizers and anti-foam agents.

The ash-producing detergents are exemplified by oil-soluble neutral and basic salts (i.e. overbased salts) of alkali or alkaline earth metals with sulfonic acids, carboxylic acids, phenols or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-beta-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60–200° C.

The oil-soluble salts of alkali or alkaline earth metal salts may also be reacted with a boron compound. Boron compounds include boron oxide, boric acid and esters of boric acid, preferably boric acid.

Patents describing techniques for making basic salts of sulfonic and carboxylic acids and mixtures thereof include U.S. Pat. Nos. 2,501,731; 2,616,911; 2,777,874; 3,384,585; 3,320,162; 3,488,284 and 3,629,109. The disclosure of these patents are hereby incorporated by reference. Borated overbased compositions, lubricating compositions contain the same and methods of preparing borated overbase compositions are found in U.S. Pat. Nos. 4,744,920; 4,792,410 and PCT publication WO 88/03144. The disclosure of these references are hereby incorporated by reference.

Ashless detergents and dispersants depending on its constitution may upon combustion yield a non-volatile material such as boric oxide or phosphorus pentoxide. However, ashless detergents and dispersants do not ordinarily contain metal and therefore do not yield a metalcontaining ash on combustion. Many types of ashless dispersants are known in the art (1) "Carboxylic dispersants" are reaction products of carboxylic acids (or derivatives thereof) containing at least about 34 and preferably at least about 54 carbon atoms are reacted with nitrogen containing compounds (such as amines), organic hydroxy compounds (such as phenols and alcohols), and/or basic inorganic materials. These reaction products include imide, amide, and ester reaction products of carboxylic acylating agents. Examples of these materials include succinimide dispersants and carboxylic ester dispersants. Examples of these "carboxylic dispersants" are described in British Patent 1,306,529 and in many U.S. Patents including the following: U.S. Pat. Nos. 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, and Re 26,433.

(2) "Amine dispersants" are reaction products of relatively high molecular weight aliphatic or alicyclic halides and amines, preferably polyalkylene polyamines. Examples thereof are described for example, in the following U.S. Pat. Nos.: 3,275,554, 3,438,757, 3,454,555, and 3,565,804.

(3) "Mannich dispersants" are the reaction products of alkyl phenols in which the alkyl group contains at least about 30 carbon atoms with aldehydes (especially formaldehyde) and amines (especially polyalkylene polyamines). The materials described in the following U.S. Patents are illustrative: U.S. Pat. Nos. 3,036,003, 3,236,770, 3,414,347, 3,448,047, 3,461,172,3,539,633, 3,586,629, 3,591,598, 3,634,515, 3,725,480, 3,726,882, and 3,980,569.

(4) Post-treated dispersants are obtained by reacting at carboxylic, amine or Mannich dispersants with reagents such as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.: 3,200,107, 3,282,955, 3,367,943, 3,513,093, 3,639,242, 3,649,659, 3,442,808, 3,455,832, 3,579,450, 3,600,372, 3,702,757,and 3,708,422.

(5) Polymeric dispersants are interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acry-lates. Examples of polymer dispersants thereof are disclosed in the following U.S. Pat. Nos.: 3,329,658, 3,449, 250, 3,519,656, 3,666,730, 3,687,849, and 3,702,300.

The above-noted patents are incorporated by reference herein for their disclosures of ashless dispersants.

Auxiliary extreme pressure agents and corrosion- and oxidation-inhibiting agents which may be included in the lubricants of the invention are exemplified by chlorinated aliphatic hydrocarbons such as chlorinated wax; sulfurized alkylphenol; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-oxidation inhibitors also serve as anti-wear agents. Zinc dialkylphosphorodithioates are a well known examples.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smallheer and R. Kennedy Smith (Lezius-Hiles Co. publishers, Cleveland, Ohio, 1967).

Examples of useful pour point depressants are polymethacrylates; polyacrylates; polyacrylamides; condensation products of haloparaffin waxes and aromatic compounds; vinyl carboxylate polymers; and terpolymers of dialkyl-fumarates, vinyl esters of fatty acids and alkyl vinyl ethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henry T. Kerner (Noyes Data Corporation, 1976), pages 125–162.

The organophosphoryl borates of the present invention may be used in lubricants or in concentrates. The concentrate might contain 0.01%, or about 0.1 to about 70% or about 80%, even up to about 90% by weight of the compositions of the present invention. These compositions may be present in a final product, blend or concentrate in any amount effective to act as an anti-wear agent, but is preferably present in the oil of lubricating viscosity, in an amount of from about 0.1 to about 10%, preferably 0.1 to about 2% by weight, most preferably about 0.25% to about 1%. In one embodiment, when the compositions of the present invention are used in oils such as gear oils, they are preferably present in an amount from about 0.1%, preferably about 1%, more preferably about 2% up to about 10%, preferably about 7%, preferably about 6% by weight of the lubricating composition.

The lubricating compositions and methods of this invention employ an oil of lubricating viscosity, including natural or synthetic lubricating oils and mixtures thereof. Natural oils include animal oils, vegetable oils, mineral lubricating oils, solvent or acid treated mineral oils, and oils derived from coal or shale. Synthetic lubricating oils include hydrocarbon oils, halo-substituted hydrocarbon oils, alkylene oxide polymers, esters of dicarboxylic acids and polyols, esters of phosphorus-containing acids, polymeric tetrahydrofurans and silicon-based oils.

The oil of lubricating viscosity is generally present in a major amount (i.e. an amount greater than 50% by weight). Preferably, the oil of lubricating viscosity is present in an amount greater than about 60%, preferably 70%, more preferably 80% by weight. In one embodiment, the oil of lubricating viscosity may be present in an amount from about 90% by weight.

Specific examples of the oils of lubricating viscosity are described in U.S. Pat. No. 4,326,972 and European Patent Publication 107,282, both herein incorporated by reference for their disclosures relating to lubricating oils. A basic, brief description of lubricant base oils appears in an article by D. V. Brock, "Lubricant Base Oils", *Lubricant Engineering*, Volume 43, pages 184–185, March, 1987. This article is herein incorporated by reference for its disclosures relating to lubricating oils. A description of oils of lubricating viscosity occurs in U.S. Pat. No. 4,582,618 (column 2, line 37 through column 3, line 63, inclusive), herein incorporated by reference for its disclosure to oils of lubricating viscosity.

In one embodiment, the oil of lubricating viscosity is selected to provide lubricating compositions of at least SAE 60 grade. Preferably, the lubricating compositions have a grade of SAE 65, more preferably SAE 75. The lubricating composition may also have a so-called multigrade rating such as SAE 60W-80, preferably 65W-80 or 65W-90, more preferably 75W-80 or 75W-90, more preferably 75W-90. Multigrade lubricants generally include a viscosity improver which is formulated with the oil of lubricating viscosity to provide the above lubricant grades. Useful viscosity improvers include polyolefins, such as polybutylene; rubbers, such as styrene-butadiene or styrene-isoprene; or polyacrylates, such as polymethacrylates. Preferably the viscosity improver is a polyolefin or polymethacrylate, more preferably polymethacrylate. Viscosity improvers available commercially include Acryloid™ viscosity improvers available from Rohm & Haas; Shellvis™ rubbers available from Shell Chemical; and Lubrizol 3174 available from The Lubrizol Corporation.

In another embodiment, the oil of lubricating viscosity is selected to provide lubricating compositions for crankcase applications, such as for gasoline and diesel engines. Typically, the lubricating compositions are selected to provide 10W, 20W, or 30W grade lubricants. The lubricating compositions may also have a so called multi-grade rating such as 10W-30, 10W-40, 20W-50, etc. As described above, multi-grade lubricants include a viscosity improver which is formulated with the oil of lubricating viscosity to provide the above lubricant grades.

The following examples relate to lubricating compositions containing the hydroxyhydrocarbyl phosphoryl borates.

EXAMPLE I

A lubricant is prepared by incorporating 3% by weight of the product of Example 1 into a SAE 10W-40 lubricating oil mixture.

EXAMPLE II

A lubricant is prepared by incorporating 2.5% by weight of the product of Example 2 into an SAE 90 lubricating oil mixture.

EXAMPLE III

A lubricant is prepared by incorporating 3% by weight of the product of Example 1, and 4% by weight of a polysulfide prepared from butylene, sulfur and hydrogen sulfide into an SAE 80W-90 lubricating oil mixture.

EXAMPLE IV

A lubricant is prepared as described in Example III except that a SAE 10W-40 lubricating oil mixture is used in place of the SAE 80W-90 lubricating oil mixture.

EXAMPLE V

A lubricant is prepared by incorporating 3% by weight the product of Example 1, and 2.5% by weight of a dithiocarbamate-containing amide is prepared from diamyl amine, carbon disulfide and acrylamide into an SAE 80W-90 lubricating oil mixture.

EXAMPLE VI

A lubricant is prepared as described in Example V except that an SAE 10W-30 lubricating oil mixture is used in place of the SAE 80W-90 lubricating oil mixture.

EXAMPLE VII

A lubricant is prepared by incorporating 3% by weight the product of Example 2, and 0.5% by weight of a succinic dispersant prepared by reacting a polybutenyl-substituted succinic anhydride, with a polybutenyl group having a number average molecular weight of about 950, with a commercial polyamine having the equivalent structure of tetraethylene pentamine into a SAE 75W-90 lubricant oil mixture.

EXAMPLE VIII

A lubricant is prepared as described in Example VII except that an SAE 10W-30 lubricating oil mixture is used in place of the SAE 75W-90 lubricant oil mixture.

EXAMPLE IX

A lubricant is prepared by incorporating 2.82% by weight of an overbased calcium alkylated benzene sulfonate (having a metal ratio of about 15 and 53% diluent as 100 neutral mineral oil and unreacted alkylated benzene); 3.3% by weight of a zinc di(2-ethylhexyl) dithiophosphate; 1% by weight of the product of Example 1 and 0.5% by weight of a carboxylic acid derivative solubilizer prepared by reacting N,N-diethylethanolamine with polybutylene succinic anhydride in a molar ratio of 1:2 wherein the polybutene succinic anhydride contains a substituent derived from a polybutene polymer having a number average molecular weight of about 1000; 1.93% by weight of a maleic anhydride-styrene copolymer esterified with $c_{8-18}$ and $C_4$ alcohols and post-treated with aminopropyl morpholine; and 0.02% by weight of a silicone anti-foam agent into an oil mixture containing 50% 250 neutral oil and 50% 65 neutral mineral oil.

EXAMPLE X

A lubricant is prepared by incorporating 2.4% of the product of Example 2; 0.3% of a polymethacrylate pour point depressant available from Shell Chemical Co. under the tradename Shellswim 140; 0.9% of oleyl amide; 0.03% of monoisopropyl amine; 0.06% of a silicone anti-foam agent; 1.9% of the reaction product of isobutylene, sulfur monochloride, sodium sulfide, and aqueous sodium hydroxide; 1.6% by weight of the reaction product of isobutylene, sulfur, and hydrogen sulfide; 0.11% of a heptylphenol dimercaptothiadiazole; and 0.75% by weight of a dimercaptothiadiazole treated reaction product of a polybutenyl succinic anhydride (equivalent weight 562) with pentaerythritol and propylene glycol which is post-treated with polyethylene amines into an oil mixture comprising 47% by weight 650 neutral mineral oil and 53% by weight 160 bright stock.

EXAMPLE XI

A lubricant is prepared by incorporating 2.2% of the product of Example 2; 1% of the maleic anhydride-styrene copolymer of Example IX; 0.06% of a silicone anti-foam agent, and 3.9% of a reaction product of isobutylene, sulfur monochloride, sodium sulfide, and an aqueous sodium hydroxide into an oil mixture composed of 75% 600 neutral mineral oil and 25% 150 bright stock.

Aqueous Compositions

The invention also includes aqueous compositions characterized by an aqueous phase with at least one product of the present invention dispersed or dissolved in said aqueous phase. Preferably, this aqueous phase is a continuous aqueous phase although, in some embodiments, the aqueous phase can be a discontinuous phase. These aqueous compositions usually contain at least about 25% by weight water. Such aqueous compositions encompass both concentrates containing about 25% to about 80% by weight, preferably from about 40% to about 65% water; and water-based functional fluids containing generally over about 80% by weight of water. The concentrates generally contain less than about 50%, preferably less than about 25%, more preferably less than about 15%, and still more preferably less than about 6% hydrocarbon oil. The water-based functional fluids generally contain less than about 15%, preferably less than about 5%, and more preferably less than about 2% hydrocarbon oil.

These concentrates and water-based functional fluids can optionally include other conventional additives commonly employed in water-based functional fluids. These other additives include surfactants; thickeners; oil-soluble, water-insoluble functional additives such as anti-wear agents, extreme pressure agents, dispersants, etc.; and supplemental additives such as corrosion-inhibitors, shear stabilizing agents, bactericides, dyes, water-softeners, odor masking agents, anti-foam agents and the like.

The water-based functional fluids may be in the form of solutions; or micelle dispersions or microemulsions which appear to be true solutions.

The surfactants that are useful in the aqueous compositions of the invention can be of the cationic, anionic, nonionic or amphoteric type. Many such surfactants of each type are known to the art. See, for example, McCutcheon's "Emulsifiers & Detergents", 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention is the alkylene oxide-treated-alkylphenols such as the ethylene oxide-alkylphenol condensates sold by the Rohm & Haas Company. A specific example of these is Triton® X-100 which contains an average of 9–10 ethylene oxide units per molecule, has an HLB value of about 13.5 and a molecular weight of about 628.

The alkoxylated amines useful as surfactants include polyalkoxylated amines and are available from Akzo Chemie under the names ETHODUOMEEN® polyethoxylated diamines; ETHOMEEN®, polyethoxylated aliphatic amines; ETHOMID®, polyethoxylated amides; and ETHOQUAD, polyethoxylated quaternary ammonium chlorides.

The acids useful as surfactants are acids derived from tall oil acids, which are distilled mixtures of acids comprising chiefly oleic and linoleic acid. Preferred tall oil acids are mixtures of rosin acids and fatty acids sold under the trade name Unitol DT/40 (available from Union Camp Corp). Many other suitable nonionic surfactants are known; see, for example, the aforementioned McCutcheon's as well as the treatise "Non-Ionic Surfactants" edited by Martin J. Schick, M. Dekker Co., New York, 1967, which is herein incorporated by reference for its disclosures in this regard.

As noted above, cationic, anionic and amphoteric surfactants can also be used. Generally, these are all hydrophilic surfactants. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, metal organosulfates, metal sulfonates, metal sulfonylcarboxylates, and metal phosphates. Useful cationic surfactants include nitrogen compounds such as amine oxides and the well-known quaternary ammonium salts. Amphoteric surfactants include amino acid-type materials and similar types. Various cationic, anionic, and amphoteric surfactants are available from the industry, particularly from such companies as Rohm & Haas and Union Carbide Corporation, both of America. Further information about anionic and cationic surfactants also can be found in the texts "Anionic Surfactants", Parts II and III, edited by W. M. Linfield, published by Marcel Dekker, Inc., New York, 1976 and "Cationic Surfactants", edited by E. Jungermann, Marcel Dekker, Inc., New York, 1976. Both of these references are incorporated by reference for their disclosures in this regard.

Surfactants are generally employed in effective amounts to aid in the dispersal of the various additives, particularly in the functional additives discussed below of the invention. Preferably, the concentrates can contain up to about 75% by weight, more preferably from about 10% to about 75% by weight of one or more of these surfactants. The water-based functional fluids can contain up to about 15% by weight, more preferably from about 0.05% to about 15% by weight of one or more of these surfactants.

Often the aqueous compositions of this invention contain at least one thickener. Generally, these thickeners can be polysaccharides, synthetic thickening polymers, or mixtures of two or more of these. Among the polysaccharides that are useful are natural gums such as those disclosed in "Industrial Gums" by Whistler and B. Miller, published by Academic Press, 1959. Disclosures in this book relating to water-soluble thickening natural gums is hereby incorporated by reference. Specific examples of such gums are gum agar, guar gum, gum arabic, algin, dextrans, xanthan gum and the like. Also among the polysaccharides that are useful as thickeners for the aqueous compositions of this invention are cellulose ethers and esters, including hydroxyhydrocarbyl cellulose and hydrocarbylhydroxy cellulose and its salts. Specific examples of such thickeners are hydroxyethyl cellulose and the sodium salt of carboxymethyl cellulose. Mixtures of two or more of any such thickeners are also useful.

It is a general requirement that the thickener used in the aqueous compositions of the present invention be soluble in both cold (10° C.) and hot (about 90° C.) water. This excludes such materials as methyl cellulose which is soluble in cold water but not in hot water. Such hotwater-insoluble materials, however, can be used to perform other functions such as providing lubricity to the aqueous compositions of this invention.

A thickener can also be synthetic thickening polymers. Many such polymers are known to those of skill in the art. Representative of them are polyacrylates, polyacrylamides, hydrolyzed vinyl esters, water-soluble homo- and interpolymers of acrylamidoalkane sulfonates containing 50 mole percent at least of acrylamidoalkane sulfonate and other comonomers such as acrylonitrile, styrene and the like.

Other useful thickeners are known to those of skill in the art and many can be found in the list in the aforementioned McCutcheon Publication: "Functional Materials," 1976, pp. 135–147, inclusive. The disclosures therein, relative to water-soluble polymeric thickening agents meeting the general requirements set forth above are hereby incorporated by reference.

Preferred thickeners, particularly when the compositions of the invention are required to be stable under high shear applications, are the water-dispersible reaction products formed by reacting at least one hydrocarbyl-substituted succinic acid and/or anhydride wherein the hydrocarbyl group has from about 8 preferably about 12, more preferably about 16, to about 40 preferably to about 30, more preferably to about 24, more preferably to about 18 carbon atoms, with at least one water-dispersible amine terminated poly (oxyalkylene) or at least one water-dispersible hydroxy-terminated polyoxyalkylene.

Examples of water-dispersible amine-terminated poly (oxyalkylene)s that are useful in accordance with the present invention are disclosed in U.S. Pat. Nos. 3,021,232; 3,108, 011; 4,444,566; and Re 31,522. The disclosures of these patents are incorporated herein by reference. Water-dispersible amine terminated poly(oxyalkylene)s that are useful are commercially available from the Texaco Chemical Company under the trade name Jeffamine®.

The water-dispersible hydroxy-terminated polyoxyalkylenes are constituted of block polymers of propylene oxide and ethylene oxide, and a nucleus which is derived from organic compounds containing a plurality of reactive hydrogen atoms. The block polymers are attached to the nucleus at the sites of the reactive hydrogen atoms. These compounds are commercially available from BASF Wyandotte Corporation under the tradename "Tetronic". Additional examples include the hydroxy-terminated polyoxyalkylenes which are commercially available from BASF Wyandotte Corporation under the tradename "Pluronic". Useful hydroxy-terminated polyoxyalkylenes are disclosed in U.S. Pat. Nos. 2,674,619 and 2,979,528, which are incorporated herein by reference.

The reaction between the succinic acid and/or anhydride and the amine- or hydroxy-terminated polyoxyalkylene can be carried out at a temperature in the range of about 60° C. to about 160° C., preferably about 120° C. to about 160° C. The ratio of equivalents of carboxylic agent to polyoxyalkylene preferably ranges from about 0.1:1 to about 8:1, preferably about 1:1 to about 4:1, and advantageously about 2:1. The reaction products may be used as salts or may form salts when added to concentrates and fluids containing metals or amines.

U.S. Pat. No. 4,659,492 is incorporated herein by reference for its teachings with respect to the use of hydrocarbyl-substituted succinic acid or anhydride/ hydroxy-terminated poly(oxyalkylene) reaction products as thickeners for aqueous compositions.

When the thickener is formed using an amine-terminated poly(oxyalkylene), the thickening characteristics of said thickener can be enhanced by combining it with at least one surfactant. Any of the surfactants identified above can be used in this regard. When such surfactants are used, the weight ratio of thickener to surfactant is generally in the range of from about 1:5 to about 5:1, preferably from about 1:1 to about 3:1.

Typically, the thickener is present in a thickening amount in the aqueous compositions of this invention. When used, the thickener is preferably present at a level of up to about 70% by weight, preferably from about 20% to about 50% by weight of the concentrates of the invention. The thickener is preferably present at a level in the range of from about 1.5% to about 10% by weight, preferably from about 3% to about 6% by weight of the functional fluids of the invention.

The functional additives that can be used in the aqueous systems are typically oil-soluble, water-insoluble additives which function in conventional oil-based systems as extreme pressure agents, anti-wear agents, load-carrying agents, dispersants, friction modifiers, lubricity agents, etc. They can also function as anti-slip agents, film formers and friction modifiers. As is well known, such additives can function in two or more of the above-mentioned ways; for example, extreme pressure agents often function as load-carrying agents.

The term "oil-soluble, water-insoluble functional additive" refers to a functional additive which is not soluble in water above a level of about 1 gram per 100 parts of water at 25° C., but is soluble in mineral oil to the extent of at least 1 gram per liter at 25° C.

These functional additives can also include certain solid lubricants such as graphite, molybdenum disulfide and polytetrafluoroethylene and related solid polymers.

These functional additives can also include frictional polymer formers. Polymer forming materials which are dispersed in a liquid are believed to polymerize under operating conditions. A specific example of such materials is dilinoleic acid and ethylene glycol combinations which can form a polyester frictional polymer film. These materials are known to the art and descriptions of them are found, for example, in the journal "Wear", Volume 26, pages 369–392, and West German Published Patent Application 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids and are described above.

Many such functional additives are known to the art. For example, descriptions of additives useful in conventional oil-based systems and in the aqueous systems of this invention are found in "Advances in Petroleum Chemistry and Refining", Volume 8, edited by John J. McKetta, Interscience Publishers, New York, 1963, pages 31–38 inclusive; Kirk-Othmer "Encyclopedia of Chemical Technology", Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smallheer and R. K. Smith, The Lezius-Hiles Co., Cleveland, Ohio, U.S.A. These references are hereby incorporated by reference for their disclosures of functional additives useful in the compositions of this invention.

The functional additive can also be a film former such as a synthetic or natural latex or emulsion thereof in water. Such latexes include natural rubber latexes and polystyrene-butadienes synthetic latex.

The functional additive can also be an anti-chatter or anti-squawk agent. Examples of the former are the amide-metal dithiophosphate combinations such as disclosed in West German Patent 1,109,302; amine salt-azomethene combinations such as disclosed in British Patent Specification 893,977; or amine dithiophosphate such as disclosed in U.S. Pat. No. 3,002,014. Examples of anti-squawk agents are N-acyl-sarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated herein by reference for their disclosure as pertinent to anti-chatter and anti-squawk agents useful as a functional additive in the aqueous systems of the present invention.

Typically, the functional additive is present in a functionally effective amount. The term "functionally effective amount" refers to a sufficient quantity of an additive to impart desired properties intended by the addition of said additive. For example, if an additive is a rust-inhibitor, a functionally effective amount of the rust-inhibitor would be an amount sufficient to increase the rust-inhibiting characteristics of the composition to which it is added.

The aqueous systems of this invention often contain at least one optional inhibitor for corrosion of either ferrous or non-ferrous metals or both. The optional inhibitor can be organic or inorganic in nature. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596–605. This disclosure relative to inhibitors are hereby incorporated by reference. Specific examples of useful inorganic inhibitors include alkali metal nitrites, sodium di- and tripolyphosphate, potassium and dipotassium phosphate, alkali metal borate and mixtures of the same. Specific examples of organic inhibitors include hydrocarbyl amine and hydroxy-substituted hydrocarbyl amine neutralized acid compounds, such as neutralized phosphates and hydrocarbyl phosphate esters, neutralized fatty acids, neutralized aromatic carboxylic acids (e.g., 4-tertiarybutyl benzoic acid), neutralized naphthenic acids and neutralized hydrocarbyl sulfonates. Particularly useful amines include the alkanolamines such as ethanolamine, diethanolamine.

The aqueous systems of the present invention can also include at least one bactericide. Such bactericides are well known to those of skill in the art and specific examples can be found in the aforementioned McCutcheon publication "Functional Materials" under the heading "Antimicrobials" on pages 9-20 thereof. This disclosure is hereby incorporated by reference as it relates to suitable bactericides for use in the aqueous compositions or systems of this invention. Generally, these bactericides are water-soluble, at least to the extent to allow them to function as bactericides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an anti-freeze additive where it is desired to use the composition at a low temperature. Materials such as ethylene glycol and analogous polyoxyalkylene polyols can be used as anti-freeze agents. Clearly, the amount used will depend on the degree of anti-freeze protection desired and will be known to those of ordinary skill in the art.

It should also be noted that many of the ingredients described above for use in making the aqueous systems of this invention are industrial products which exhibit or confer more than one property on such aqueous compositions. Thus, a single ingredient can provide several functions thereby eliminating or reducing the need for some other additional ingredient. Thus, for example, an extreme pressure agent such as tributyl tin oxide can also function as a bactericide.

Discussion of aqueous compositions and components of aqueous systems occurs in U.S. Pat. No. 4,707,301, herein incorporated by reference for its disclosure of aqueous compositions and components of aqueous compositions.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed:

1. An aqueous composition comprising water, a minor extreme pressure or antiwear improving amount of a borate ester represented by one of the following formulae:

$$((R_1)_2P(X_2)X_1R_2O)_3B \quad \text{or}$$

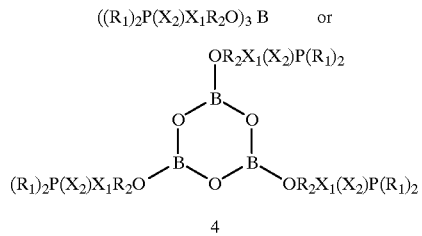

wherein each $R_1$ is independently hydrogen, a hydrocarbyl, a hydrocarbyloxy or a hydrocarbylthio group or both $R_1$ on the same phosphorus atom taken together form a hetrocyclic group; each $X_1$ and $X_2$ is independently an oxygen or sulfur, provided that at least one of $X_1$ or $X_2$ is sulfur; and each $R_2$ is independently a hydrocarbylene group, provided that at least one $R_1$ is other than hydrogen.

2. The composition of claim 1, wherein each $R_1$ independently contains from one to about 30 carbon atoms.

3. The composition of claim 1, wherein each $R_1$ is independently derived from an alcohol or phenol.

4. The composition of claim 1, wherein each $R_1$ is independently derived from propyl alcohol, butyl alcohol, amyl alcohol, methylamyl alcohol, cyclopentyl alcohol, cyclohexyl alcohol, 2-ethylhexyl alcohol, octyl alcohol, heptyl phenol, tetrapropenylphenol or cresol.

5. The composition of claim 1, wherein at least one of $X_1$ and $X_2$ is sulfur or at least one $R_1$ is a hydrocarbylthio group.

6. The composition of claim 1, wherein $X_1$ and $X_2$ are sulfurs.

7. The composition of claim 1, wherein $X_1$ and $X_2$ are oxygens.

8. The composition of claim 1, wherein each $R_2$ is independently an alkylene having from one to about 30 carbon atoms or an arylene group having six to about 30 carbon atoms.

9. The composition of claim 1, wherein each $R_2$ is independently derived from ethylene oxide, propylene oxide, butylene oxide, cyclohexene oxide, styrene oxide, decene oxide, tetradecene oxide, hexadecene oxide, or octadecene oxide.

10. The composition of claim 1, wherein the borate ester is prepared by reacting (A) a hydroxy-containing organophosphorus compound, having at least one sulfur atom, with (B) a boron compound, wherein the mixture is substantially free of dihydroxy phosphorus-free alcohols and dihydroxy fatty carboxylic esters, and at least one sulfurized organic composition or a dithiocarbamate-containing compound.

11. The composition of claim 10, wherein the hydroxy-containing organophosphorus compound (A) is prepared by reacting an organophosphorus acid with an epoxide.

12. The composition of claim 11, wherein the organophosphorus acid is an organo mono-, di, tri- or tetra-thiophosphoric acid.

13. The composition of claim 11, wherein the organophosphorus acid is an organothiophosphorus acid prepared by reacting a phosphorus sulfide with at least one alcohol or phenol.

14. The composition of claim 13, wherein the alcohol contains from one to about 30 carbon atoms and the phenol contains six to about 30 carbon atoms.

15. The composition of claim 13, wherein the alcohol is independently selected from propyl alcohol, butyl alcohol, amyl alcohol, methylamyl alcohol, cyclo-pentyl alcohol, cyclohexyl alcohol, 2-ethylhexyl alcohol, octyl alcohol, heptylphenol, tetrapropenylphenol, and cresol.

16. The composition of claim 11, wherein the epoxide is selected from ethylene oxide, propylene oxide, butylene oxide, cyclohexene oxide and styrene oxide, decene oxide, tetradecene oxide, hexadecene oxide and octadecene oxide.

17. The composition of claim 11, wherein the epoxide is ethylene or propylene oxide.

18. The composition of claim 10, wherein (B) the boron compound is boric acid.

19. The composition of claim 1, wherein the borate ester is prepared by reacting a hydroxy-containing organophosphorus compound, having at least one sulfur atom with a boron compound, and the composition further comprises at least one sulfurized organic composition or a dithiocarbamate-containing compound.

20. The composition of claim 19, wherein the sulfurized organic compound is a sulfurized compound selected from olefins, fatty acids, fatty oils, fatty esters, terpines, Diels-Alder adducts and mixtures thereof, and wherein the dithiocarbamate-containing compound is selected from hydrocarbylene-coupled dithiocarbamates, sulfur-coupled dithiocarbamates and reaction products of dithiocarbamic acids or salts thereof with unsaturated acids, esters or amides.

21. The composition of claim 19, further comprising at least one extreme pressure agent, dispersant, or detergent.

22. The aqueous composition of claim 1 wherein the composition further comprises at least one surfactant or thickener.

* * * * *